(12) United States Patent
Gonin et al.

(10) Patent No.: US 10,444,186 B2
(45) Date of Patent: Oct. 15, 2019

(54) METHOD AND AN APPARATUS FOR DETERMINING A SPECTRUM

(71) Applicant: TOFWERK AG, Thun (CH)

(72) Inventors: Marc Gonin, Thun (CH); Christian Tanner, Olten (CH)

(73) Assignee: TOFWERK AG, Thun (CH)

( * ) Notice: Subject to any disclaimer, the term of this patent is extended or adjusted under 35 U.S.C. 154(b) by 122 days.

(21) Appl. No.: 15/730,251

(22) Filed: Oct. 11, 2017

(65) Prior Publication Data
US 2018/0100830 A1  Apr. 12, 2018

(30) Foreign Application Priority Data

Oct. 12, 2016 (EP) ..................................... 16193562

(51) Int. Cl.
*H01J 49/00* (2006.01)
*G01N 27/62* (2006.01)

(52) U.S. Cl.
CPC ........ *G01N 27/622* (2013.01); *H01J 49/0036* (2013.01); *H01J 49/0072* (2013.01)

(58) Field of Classification Search
CPC .... H01J 49/00; H01J 49/0004; H01J 49/0009; H01J 49/0027; H01J 49/0031;
(Continued)

(56) References Cited

U.S. PATENT DOCUMENTS 7,417,222 B1  8/2008 Pfeifer et al.
2004/0144918 A1  7/2004 Zare et al.
(Continued)

FOREIGN PATENT DOCUMENTS

| EP | 2 587 259 A1 | 5/2013 |
|---|---|---|
| EP | 2 698 621 A1 | 2/2014 |
| WO | WO 98/08244 A2 | 2/1998 |

*Primary Examiner* — Jason L McCormack
(74) *Attorney, Agent, or Firm* — Birch, Stewart, Kolasch & Birch, LLP

(57) ABSTRACT

The invention relates to a method and an apparatus for determining a spectrum of a sample comprising one or more constituent parts on the basis of a time the one or more constituent parts require to undergo a physical process or chemical process. The spectrum is determined by dividing the sample by a modulation unit into assays for which the physical process or chemical process is initiated successively, timed according to a modulation pattern which is a function composed of N consecutive modulation functions with N being 2 or larger, by measuring with a detector in N consecutive cycles a time when the constituent parts of the sample have completed the physical process or chemical process, wherein in succession of the cycles, each cycle is assigned to a consecutive one of the modulation functions within the modulation pattern, wherein each cycle is started with an offset in time as compared to a start of the modulation function it is assigned to, wherein for each cycle, the offset is different, wherein the detector provides a detector signal providing information on when what number of constituent parts have completed the physical process or chemical process and wherein the detector signal has a detection time resolution, wherein at least one of the offsets has an absolute value different from zero, different from the detection time resolution and different from multiples of the detection time resolution, and by calculating a correlation of the detector signal and the modulation pattern with a calculation unit.

19 Claims, 2 Drawing Sheets

(58) Field of Classification Search
CPC .... H01J 49/0036; H01J 49/0045; H01J 49/02; H01J 49/025; G01N 27/622
USPC ........................................ 250/281, 282, 283
See application file for complete search history.

(56) References Cited

U.S. PATENT DOCUMENTS

| | | |
|---|---|---|
| 2008/0185513 A1 | 8/2008 | Belov et al. |
| 2009/0294647 A1 | 12/2009 | Michelmann |
| 2015/0060656 A1* | 3/2015 | Ugarov ................. H01J 49/061 250/282 |

* cited by examiner

METHOD AND AN APPARATUS FOR DETERMINING A SPECTRUM

TECHNICAL FIELD

The invention relates to a method and an apparatus for determining a spectrum of a sample comprising one or more constituent parts on the basis of a time the one or more constituent parts require to undergo a physical process or chemical process.

BACKGROUND ART

Methods and apparatuses pertaining to the above mentioned technical field are known. US 2009/0294647 A1 (Karsten Michelmann) for example describes an ion mobility spectrometer which is coupled to a mass spectrometer and a corresponding measuring method. In this example, the sample comprises ions. A beam of these ions is modulated according to a continuous modulation function, wherein the modulation frequency of the modulation function is varied over a large frequency range. For a measurement, the modulated ion beam is passed through a drifting region, after what the ions are detected with the mass spectrometer serving as detector for the ion mobility spectrometer. In order to obtain the ion mobility spectrum, the detector signal provided by the detector is correlated with the modulation function according to which the ion beam was initially modulated.

Another ion mobility spectrometer and corresponding method are disclosed in U.S. Pat. No. 7,417,222 B1 (Sandia Corp). There as well, the ion beam is modulated according to a modulation function and the measured signal is correlated with the modulation function. But in contrast to US 2009/0294647 A1, the modulation function may also be a binary function.

These known methods and apparatuses have in common that the sample comprises ions. A beam of these ions is modulated according to a modulation function. After this modulation, the ions are passed through a drifting region and are detected at the end of the drifting region by a detector which provides a detector signal. By calculating a correlation of the modulation function with the detector signal, the ion mobility spectrum is obtained. This procedure for obtaining the ion mobility spectra is employed because it is not required to know the starting time of each individual ion as it would be if directly measuring the ion's flight time. Consequently, it is possible to pass at the same time more than one pulse or packet of ions through the drifting region. This has the advantage that the ion mobility of more ions can be measured within the same period of time, thus enabling a higher data collection rate.

The disadvantage of these methods and apparatuses is however that the resolution of the measured spectra is limited.

SUMMARY OF THE INVENTION

It is the object of the invention to create a method and an apparatus pertaining to the technical field initially mentioned that enables determining a spectrum with a better resolution and a high data collection rate.

The solution of the invention is specified by the features of claim 1. According to the invention, the spectrum is determined by dividing the sample by a modulation unit into assays for which the physical process or chemical process is initiated successively, timed according to a modulation pattern which is a function composed of N consecutive modulation functions with N being 2 or larger, by measuring with a detector in N consecutive cycles a time when the constituent parts of the sample have completed the physical process or chemical process, wherein in succession of the cycles, each cycle is assigned to a consecutive one of the modulation functions within the modulation pattern, wherein each cycle is started with an offset in time as compared to a start of the modulation function it is assigned to, wherein for each cycle, the offset is different, wherein the detector provides a detector signal providing information on when what number of constituent parts have completed the physical process or chemical process and wherein the detector signal has a detection time resolution, wherein at least one of the offsets has an absolute value different from zero, different from the detection time resolution and different from multiples of the detection time resolution, and by calculating a correlation of the detector signal and the modulation pattern with a calculation unit.

The apparatus according to the invention comprises a modulation unit for dividing the sample into assays for which the physical process or chemical process is initiatable successively, timed according to a modulation pattern which is a function composed of N consecutive modulation functions with N being 2 or larger. Furthermore, the apparatus comprises a detector for measuring in N consecutive cycles a time when the constituent parts of the sample have completed the physical process or chemical process, wherein in succession of the cycles, each cycle is assigned to a consecutive one of the modulation functions within the modulation pattern, wherein the detector enables starting each cycle with an offset in time as compared to a start of the modulation function it is assigned to, wherein for each cycle, the offset is different, wherein a detector signal is providable by the detector, the detector signal providing information on when what number of the constituent parts have completed the physical process or chemical process, wherein the detector signal has a detection time resolution, wherein at least one of the offsets has an absolute value different from zero, different from the detection time resolution and different from multiples of the detection time resolution. Additionally, the apparatus comprises a calculation unit for calculating a correlation of the detector signal and the modulation pattern.

As initially mentioned, the sample comprises one or more constituent parts. These constituent parts may for example be particles like aerosols, molecules or ions and have a common physical or chemical property. The physical property may for example be the mass, mass per charge ratio, mobility or the time taken for passing a gas chromatography column. The chemical property may for example be the time the constituent parts take to undergo a specific chemical reaction. In either case, the magnitude of the common property may be different for different constituent parts of the sample.

In the context of the present invention, the term spectrum refers to an array of data points and represents the one or more constituent parts of the sample ordered in accordance with the magnitudes of a common chemical or physical property. Each data point is assigned to a particular magnitude or a particular range of magnitudes of the common chemical or physical property and each data point indicates the amount of constituent parts in the sample which have a magnitude of the common chemical or physical property matching the particular magnitude or being within the particular range of magnitudes assigned to the respective data point.

Thus, the spectrum with its data points provides information on the distribution of the one or more constituent parts in the sample with respect to the constituent parts' magnitudes of the common chemical or physical property. In order to provide this information, the data points are not required to express the exact quantity of constituent parts having a magnitude of the chemical or physical property matching the particular magnitude or being within the particular range of magnitudes assigned to the respective data point. Rather, it is sufficient for the data points to provide a number which is proportional to the exact quantity, thus indicating the amount of constituent parts. Thus, each data point in the spectrum may be a single number. In this case, each single number indicates the amount of constituent parts having a magnitude of the common chemical or physical property matching the particular magnitude or being within the particular range of magnitudes assigned to the respective data point. In a variant, each data point in the spectrum may comprise two numbers. In this case, the first number of each data point indicates the amount of constituent parts having the magnitude of the common chemical or physical property matching the particular magnitude or being within the particular range of magnitudes assigned to the respective data point, while the second number of each data point indicates the magnitude or range of magnitudes of the chemical or physical property the respective data point is assigned to.

According to the invention, the sample is divided by a modulation unit into assays for which the physical process or chemical process is initiated successively, timed according to the modulation pattern. As for the magnitudes of the common physical or chemical property of the constituent parts, these assays preferably comprise essentially the same distribution of constituent parts as the sample. In a variant, the assays comprise, as for the magnitudes of the common physical or chemical property of the constituent parts, the same distribution of constituent parts as the sample. Depending on the efficiency of the modulation unit, deviations from exactly the same distribution may however occur. In a preferred variation however, the assays comprise as for the magnitudes of the common physical or chemical property of the constituent parts a similar distribution of constituent parts as the sample, wherein the distribution may change over time from assay to assay.

In an example where the spectrum is an ion mobility spectrum, the sample may comprise the ions in an ion beam. This ion beam is modulated into a modulated ion beam by a modulation unit formed by an ion gate. In this case, the modulated ion beam comprises batches or bunches of ions, the batches or bunches being assays comprising essentially the same distribution of constituent parts as the sample. For these assays, the physical process of passing the drifting region is initiated by the modulation unit, i.e. the ion gate, successively, timed according to the modulation pattern.

In another example where the spectrum is a gas chromatogram, the sample may for example have the form of a liquid or a gas. In case of a liquid sample, the sample may be divided into assays by an injection unit which injects the assays successively, timed according to the modulation pattern into an evaporation chamber or directly into a gas chromatography column if the evaporation chamber is integrated in the gas chromatography column. In the evaporation chamber, the physical process of passing the gas chromatography column is initiated by evaporating the liquid. In another variant, the entire sample may be introduced into the evaporation chamber in one go. In this variant, the sample may be divided into assays by a heating device which heats the sample with heating pulses timed according to the modulation pattern. Thus, the employed heating device forms the modulation unit and initiates the physical process of passing the gas through the gas chromatography column. On the other hand, in case of a gaseous sample, the modulation unit may be a gas inlet which divides the sample into assays by injecting pulses of gas into the gas chromatography column. In this case, the physical process of passing the gas chromatography column is initiated with the injection of the pulses into the gas chromatography column.

Besides the above mentioned examples of the spectrum being an ion mobility spectrum or a gas chromatogram, the spectrum determined by the method and the apparatus according to the invention may be a different kind of spectrum. For example, it may be an aerosol mobility spectrum, a liquid chromatogram, a mass spectrum or even any another kind of spectrum which can be determined on the basis of the time the one or more constituent parts of the sample require to undergo a physical process or chemical process.

According to the invention, the modulation pattern is a function composed of N consecutive modulation functions with N being 2 or larger. Thus, as the physical process or chemical process is initiated for the assays successively, timed according to the modulation pattern, the physical process or chemical process is initiated successively, timed sequentially according to the modulation functions within the modulation pattern. It is first initiated timed according to the first modulation function within the modulation pattern and second according to the second modulation function within the modulation pattern. If there are further modulation functions within the modulation pattern, it is subsequently initiated successively, timed sequentially according to the remaining modulation functions within the modulation pattern. In this operating sequence, each time the physical process or chemical process starts to get initiated timed according to another one of the modulation functions within the modulation pattern is considered as a start of the respective modulation function.

According to the invention, the time when the constituent parts of the sample have completed the physical process or chemical process is measured with a detector in N consecutive cycles. In succession of these cycles, each of the cycles is assigned to a consecutive one of the modulation functions within the modulation pattern. Thereby, the cycles may follow each other immediately or there may be time gaps between them. In either case, each cycle is started with an offset in time as compared to the start of the modulation function it is assigned to, wherein for each cycle, the offset is different. In a first preferred variant, one of these offsets is zero while the other offsets are larger than zero. In a second preferred variant, all the offsets are larger than zero. Thus, in an example, one of the cycles is started together with the modulation function it is assigned to, while each one of the other cycles is started later than the modulation function the respective cycle is assigned to. In another example, each one of the cycles is started later than the modulation function the respective cycle is assigned to. In an alternative however, some or all offsets may be negative.

Each cycle is started with the detector starting to collect data for the respective cycle by measuring the time when the constituent parts of the sample have completed the physical or chemical process. Consequently, for each cycle, the detector starts to collect data with the respective offset in time as compared to the start of the modulation function the respective cycle is assigned to.

According to the invention, the detector provides a detector signal providing information on when what number of the constituent parts have completed the physical process or chemical process. Since the detector measures in N consecutive cycles the time when the constituent parts of the sample have completed the physical process or chemical process, the detector provides for each cycle a detector signal which is attributed to the respective cycle. In a variant, the detector signal of the different cycles may be provided as separate detector signals. In another variant, the detector signal of the different cycles may be provided in form of one detector signal. In the latter variant, the detector signals of the different cycles are cutouts from the one detector signal provided by the detector. These cutouts are identified with the start and the duration of the respective cycle.

The detector signal as provided by the detector has a detection time resolution. This detection time resolution is the resolution in time with which the detector signal provides the information on when what number of constituent parts have completed the physical process or chemical process. Preferably, the detector provides the detector signal in the form of discrete data points. In this case, each data point provides information on the number of constituent parts which have completed the physical or chemical process within a specific time interval associated to the respective data point. In order to provide this data point in the detector signal, the detector continuously collects data for the time interval associated to the respective data point.

For a detector signal in the form of discrete data points, the detection time resolution is the time span between the beginning of the specific time interval associated to one data point and the beginning of the specific time interval associated to the next following data point within the detector signal. Thus, it is irrelevant for the detection time resolution whether there is a time gap between the time intervals associated to two consecutive data points or whether the time intervals associated to two consecutive data points succeed each other without any time gap in between.

Preferably, the detection time resolution is provided in time units. The smaller the detection time resolution is in time units, the better the detection time resolution is. The larger the detection time resolution is in time units, the worse it is.

Since the time the constituent parts require to undergo the physical or chemical process may be larger than a time gap between the initiations of the physical or chemical process for two succeeding assays, the constituent parts of more than one assay may be undergoing the physical or chemical process at the same time. Therefore, the detector signal which provides information on when what number of constituent parts have completed the physical or chemical process does not directly indicate from which assay the detected constituent parts origin. However, by calculating the correlation of the detector signal and the modulation pattern with the calculation unit, the spectrum can be determined. In particular, the correlation yields the spectrum. Either, the correlation is the spectrum or the correlation is further treated to become the spectrum. In the latter case, the correlation may for example be filtered with a mathematical filter in order to become the spectrum.

As mentioned already, the cycles are started with different offsets in time as compared to the start of the modulation function they are respectively assigned to. According to the invention, at least one of these offsets has an absolute value different from zero, different from the detection time resolution and different from multiples of the detection time resolution. Due to this at least one of the offsets which has an absolute value which is at the same time different from zero, different from the detection time resolution and different from multiples, i.e. integer multiples of the detection time resolution, the detector signal of all cycles enables to provide a spectrum with an improved resolution. Consequently, the solution according to the invention has the advantage that it enables to determine the spectrum with a better resolution at a high data collection rate.

Advantageously, for each modulation function within the modulation pattern, an autocorrelation of the respective modulation function is a two-valued function, wherein the autocorrelation has a peak at zero and a constant value at all other points. This has the advantage that calculating the correlation does not introduce additional features into the ion mobility spectra.

Alternatively, for each modulation function within the modulation pattern, an autocorrelation of the respective modulation function is a function which has a peak or high value at zero and a lower value at all other points.

Preferably, each modulation function within the modulation pattern is a binary function. Accordingly, the modulation functions and thus the modulation pattern may be represented by a row of bits. This has the advantage that it is simple to divide the sample with the modulation unit into assays for which the physical or chemical process is initiated successively, timed according to the modulation pattern. In a variant, each modulation function within the modulation pattern is based on a binary function but provides smoothed steps between the bits of the binary function. This has the advantage that a non-perfect efficiency of the modulation unit can be taken into account for by adapting the modulation functions accordingly. Alternatively, one or more of the modulation functions within the modulation pattern is a non-binary function.

In the following, there are passages where the modulation functions within the modulation pattern are described as being binary functions or sequences. In these passages, the modulation functions may effectively be the described binary functions or sequences. But they may as well be functions which are based on the described binary functions or sequences. In the latter case, the modulation functions may provide smoothed steps between the bits of the described binary functions or sequences.

Advantageously, each modulation function within the modulation pattern is a pseudorandom sequence. This has the advantage that the properties of the modulation functions approximate the properties of random sequences. Therefore, repetitions in the modulation functions that would lead to additional peaks in the spectrum can be avoided if the length of the pseudorandom sequences is chosen accordingly. Furthermore, pseudorandom sequences as modulation functions have the advantage that the modulation functions can easily be generated like for example with a linear feedback shift register.

If the modulation functions within the modulation pattern are pseudorandom sequences of a type known as maximum length sequences or of a type that can be represented by one or more maximum length sequences, it is advantageous to use a linear feedback shift register for generating the modulation functions within the modulation pattern. In this case, the apparatus according to the invention preferably comprises a linear feedback shift register for generating the modulation functions within the modulation pattern. In such a linear feedback shift register, a number of feedback patterns are possible, called tap sets of the linear feedback shift register. The number of possible tap sets depends on the length of the particular linear feedback shift register. The modulation functions are generated with the linear feedback shift register by choosing a tap set and a set of initial values. The set of initial values is fed to the linear feedback shift register. Based on the set of initial values, the modulation function is then generated by the linear feedback shift register according to the tap set. Therefore, the modulation functions depend on the tap set and on the set of initial values. Since there are two or more modulation functions within the modulation pattern, all modulation functions may be generated with the same linear feedback shift register. In case the tap set the set of initial values is chosen to be the same for each modulation function, the modulation functions are the same. In case the tap set and/or the set of initial values are chosen to be different for each one of the modulation functions, the resulting modulation functions differ from each other. There is however as well the option that some or all of the modulation functions within the modulation pattern are generated by different linear feedback shift registers.

As a variant, one or all modulation functions within the modulation pattern may be generated in a different way. For example, one or more known pseudorandom sequences or other modulation functions may be stored in a data store. For each measurement, modulation functions stored in the data store may be used. In such a variant, the apparatus does not require to comprise a linear feedback shift register. It may then for example comprise a data store for storing one or more known pseudorandom sequences or other modulation functions.

In a further variant, the modulation functions within the modulation pattern may be different functions than pseudorandom sequences. For example, they may be random sequences. This has the advantage that the functions have the corresponding properties. Alternatively, the modulation functions within the modulation pattern may be non-random functions.

Preferably, each modulation function within the modulation pattern is a maximum length sequence, a GMW sequence, a Welch-Gong transformation sequence, a Quadratic residue sequence, a Sextic residue sequence, a Twin prime sequence, a Kasami power function sequence, a Hyperoval sequence or a sequence derived from 3 or 5 maximum length sequences. This has the advantage that the modulation functions are sequences with well known properties. In case one of the sequences is derived from 3 to 5 maximum length sequences, it may for example be obtained by adding up the content of corresponding bits of the 3 or 5 maximum length sequences. In that case, the addition of two 1s or of two 0s may result in a 0, while the addition of a 0 and a 1 or of a 1 and a 0 may result in a 1 (bitwise NAND operation).

As a variant, the modulation functions within the modulation pattern may be pseudorandom sequences which do not belong to one of these classes.

Preferably, if the modulation functions within the modulation pattern are binary functions or sequences, they have a length of more than 15 bits, preferably more than 50 bits, in particular more than 100 bits. This has the advantage that the modulation functions are long enough to enable measurements where sufficient constituent parts of the sample are being measured for obtaining meaningful spectra.

Alternatively, one, more than one or all of the modulation functions within the modulation pattern may have a length of 15 bits or less. This may be advantageous if the time of a measurement should be short.

Advantageously, all modulation functions within the modulation pattern have a same length. Thus, initiating the physical or chemical process timed according to the modulation functions takes for each modulation function a same amount of time. This enables measuring the time when the constituent parts of the sample have completed the physical or chemical process with the detector in cycles having a same length in time while at the same time using the sample optimally.

Alternatively, only some of the modulation functions or none of the modulation functions may have a same length.

Advantageously, all modulation functions within the modulation pattern are the same. This has the advantage that the handling of the modulation functions becomes simpler.

Alternatively, only some of the modulation functions or none of the modulation functions within the modulation pattern may differ from each other.

Advantageously, the offsets differ from each other, wherein a difference between any two of the offsets is one fraction of the detection time resolution or a multiple of the one fraction of the detection time resolution. In a preferred variant, all offsets differ from each other, wherein a difference between any two of the offsets is one fraction of the detection time resolution or a multiple of the one fraction of the detection time resolution. Either variant has the advantage that based on a given detection time resolution and a given number N, the spectrum can be determined with an improved resolution.

Preferably, the one fraction of the detection time resolution is the detection time resolution divided by N. This has the advantage that based on a given detection time resolution and a given number N, the spectrum can be determined with an optimal resolution.

Alternatively, the offsets may differ differently from each other.

Advantageously, the detection time resolution of the detector signal of each cycle is the same. This has the advantage that the detector signals of the different cycles are better comparable.

Alternatively, the detection time resolution of the detector signals of some or all cycles may be different.

Preferably, the detector signal is an array of data points, wherein each data point provides information on the number of the constituent parts which have completed the physical process or chemical process within a time interval assigned to the respective data point. In order to provide one data point in the detector signal, the detector continuously collects data for the time interval associated to the respective data point. Preferably, the time intervals are arranged consecutively in time. Advantageously, all time intervals have a same length. Alternatively, the time intervals may however have different lengths. Preferably, the length of the time intervals is equal to the detector time resolution divided by N or smaller than the detector time resolution divided by N. In the latter case, consecutive time intervals are preferably arranged consecutively with equal time gaps between succeeding time intervals. Alternatively, consecutive time intervals may be arranged consecutively with different time gaps between succeeding time intervals.

As an alternative to the detector signal being an array of data points, the detector signal may be an analogue and thus continuous signal like for example a voltage.

Preferably, the correlation is calculated by calculating a circular cross correlation, an inverse Hadamard-transformation, a Fourier transformation, a Laplace transformation or an M-transformation. This has the advantage that the correlation is calculated by a known formalism. Alternatively, a different formalism may be employed as well for calculating the correlation.

Independent of whether the detector signal is an array of data points or an analogue and thus continuous signal, for calculating the correlation of the detector signal and the modulation pattern, preferably each cycle and the modulation function the respective cycle is assigned to are treated as an entity having a local timeline. Furthermore, for each entity, the modulation function of the respective entity preferably starts on the local timeline of the respective entity at a predetermined time which is for all entities the same. As a result, on the local timeline, the respective entity's cycle starts at the respective cycle's offset after the start of the respective entity's modulation function. For calculating the correlation of the detector signal and the modulation pattern, the detector signal of each cycle is preferably considered as a separate signal of the respective cycle and thus of the entity the respective cycle belongs to, wherein each of the separate signals starts with the corresponding cycle. This may for example be achieved in that for the separate signal of each cycle, an initial delay corresponding to the respective cycle's offset in time as compared to the start of the modulation function the respective cycle is assigned to is prefixed to the separate signal of the respective cycle before the correlation is calculated. In this example, on the local timeline of an entity, the respective entity's modulation function and the prefixed initial delay of the detector signal of the respective entity's cycle start at the same predetermined time.

In a first preferred variant, the correlation of the detector signal and the modulation pattern is calculated with the calculation unit by first correlating for each entity the separate signal of the respective entity with the respective entity's modulation function in order to obtain for each entity an array of data points, by second providing each array of data points on the local timeline of the respective entity and by third treating the local timelines of the entities as being the same and combining the data points of the obtained arrays to one array of data points which is the correlation.

In a second preferred variant, the correlation of the detector signal and the modulation pattern is calculated with the calculation unit by first providing for each entity the separate signal of the respective entity on the local timeline of the respective entity, by second treating the local timelines of the entities as being the same and combining the separate signals of the entities to one virtual signal and by third correlating the virtual signal with one of the modulation functions within the modulation pattern, wherein the modulation functions within the modulation pattern are the same.

In these two variants of calculating the correlation of the detector signal and the modulation pattern, the data points of the obtained arrays or the separate signals, respectively, are provided on the local timeline of their respective entity when being combined, while the local timelines are treated as being the same. Thus, treating the local timelines as being the same and combining the data points or separate signals, respectively, means using the values of the positions of the data points or of the separate signals, respectively, which refer to the respective local timeline, and applying these values to a new, globally valid timeline. Thus, for example, two data points of a first entity which are on the first entity's local timeline positioned at 0.5 time units and 1.0 time units and two other data points of a second entity which are on their second entity's local timeline positioned at 0.75 time units and 1.25 time units get combined at 0.5, 0.75, 1.0 and 1.25 time units, respectively, of the new, globally valid timeline. Thus, the data points or separate signals of the different entities get preferably interlocked when being combined.

The first preferred variant for calculating the correlation of the detector signal and the modulation pattern has the advantage that different modulation functions within the modulation pattern may be employed. The second preferred variant for calculating the correlation of the detector signal and the modulation pattern however has the advantage that the calculation of the correlation takes less time.

In either variant of calculating the correlation of the detector signal and the modulation pattern, for each entity, the predetermined time at which the modulation function of the respective entity starts on the local timeline of the respective entity is preferably zero. This has the advantage that treating the local timelines of the entities as being the same provides a correlation which can directly be identified as the spectrum to be determined. In an alternative, for each entity, the predetermined time at which the modulation function of the respective entity starts on the local timeline of the respective entity may be a non-zero value. In this case, the timeline of the calculated correlation is to be shifted by this non-zero value in order to obtain the spectrum to be determined from the correlation.

Furthermore, in either variant of calculating the correlation of the detector signal and the modulation pattern, in case the detector signal is an array of data points and for each point, the detector continuously collects data for a time interval associated to the respective data point, the time intervals associated to the data points are preferably shorter than the detector time resolution divided by N.

In an alternative to the above described two ways of calculating the correlation of the detector signal and the modulation pattern, the correlation may be calculated by directly correlating the detector signal with the modulation pattern. In this case, the detector signal of the different cycles is advantageously provided in the form of one detector signal. Advantageously, the detector signal is in a first step correlated with the modulation pattern in order to obtain an array of data points. In a second step, cutouts of the obtained array of data points are defined, wherein the cutouts have a length corresponding to the lengths of the modulation functions within the modulation pattern and wherein the cutouts have a sequential arrangement corresponding to the sequential arrangement of the modulation functions within the modulation pattern. And in a third step, the data points of the cutouts are combined to one array being the correlation by assuming that each cutout has its own timeline on which the respective cutout starts at a predetermined time which is for all cutouts the same, wherein the cutouts are provided on their respective local timeline, wherein the local timelines of the cutouts are treated as being the same when the cutouts are combined to the one array being the correlation. In this alternative, the predetermined time at which the cutouts start on their respective local timeline is preferably zero. In case the predetermined time is a non-zero value, the timeline of the obtained one array is to be shifted by this non-zero value in order to obtain the spectrum to be determined from the correlation. Furthermore, in this alternative, the autocorrelation of the modulation pattern is preferably a two-valued function, wherein the autocorrelation has a peak at zero and a constant value at all other points, or a function which has a peak or high value at zero and a lower value at all other points.

Preferably, each modulation function within the modulation pattern has a modulation time resolution. This modulation time resolution is the resolution in time with which the physical or chemical process is initiated for the assays successively, timed according to the modulation functions within the modulation pattern. It is one of the factors which determine the minimal width in time of the peaks which can be resolved in the spectra to be determined.

Since the physical process or chemical process is initiated for the assays successively, timed sequentially according to the modulation functions within the modulation pattern, each modulation function within the modulation pattern is assigned to some of the assays. For example, each modulation function within the modulation pattern determines for each one of the assays to which the respective modulation function is assigned the time duration during which the physical process or chemical process is initiated for the respective assay. In one variant, this time duration is the same for all assays to which one of the modulation functions is assigned. In another variant, this time duration however is different for different assays to which one of the modulation functions is assigned.

The time duration during which the physical process or chemical process is initiated for the assays influences the minimal width in time of the peaks which can be resolved in the spectrum to be determined by the method and the apparatus according to the invention. Thus, for each one of the modulation functions within the modulation pattern, the modulation time resolution is preferably the shortest time duration during which the physical process or chemical process is initiated for one of the assays to which the respective modulation function is assigned.

Preferably, the modulation time resolution is provided in time units. The smaller the modulation time resolution in time units is, the better the modulation time resolution is, since it enables a more precise determination of the spectrum. The larger the modulation time resolution in time units is, the worse it is.

Advantageously, the modulation time resolution of each modulation function within the modulation pattern is the same. This has the advantage that the minimal width in time of the peaks which can be resolved in the spectra is optimally determined. Alternatively however, the modulation time resolution of the different modulation functions within the modulation pattern may be different.

Preferably, the modulation time resolution is at least three times, preferably at least five times, particularly preferably at least seven times or ten times larger than the detection time resolution. This has the advantage that the spectrum can be determined with an optimal resolution.

Preferably, the cycles have a same duration in time. This has the advantage that the calculation of the correlation is simplified and that determining one spectrum takes less time.

Alternatively, the cycles may however have different durations in time.

Advantageously, the spectrum is an ion mobility spectrum, an aerosol mobility spectrum or an aerosol size distribution, a gas chromatography spectrum or a liquid chromatography spectrum. In this case, the apparatus according to the invention is preferably an ion mobility spectrometer, an aerosol mobility spectrometer, a gas chromatography spectrometer or a liquid chromatography spectrometer. In case of an aerosol mobility spectrometer, the aerosol mobility spectrometer may provide an aerosol mobility spectrometer from which an aerosol size distribution can be derived or the aerosol mobility spectrometer may provide directly an aerosol size distribution or an aerosol mobility spectrum as well as an aerosol size distribution. For obtaining the aerosol size distribution from the aerosol mobility spectrum, preferably the gas, the gas pressure in the drifting region and the length of the drifting path in the drifting region are considered in a way as known in the art.

Alternatively, the spectrum to be determined is a different type of spectrum. In this case, the apparatus according to the invention is a different type of spectrometer.

Preferably, the detector is an ion mobility spectrometer or a mass spectrometer, in particular a time-of-flight mass spectrometer. Alternatively, the detector is a different type of spectrometer or no spectrometer as long as it is a detector which enables measuring the time when the constituent parts of the sample have completed the physical or chemical process.

In case the detector requires ions for its measurements like for example in the case where the detector is an ion mobility spectrometer or a mass spectrometer, the ions have to be provided. In case the constituent parts of the sample are already ions like in the case where the spectrum to be determined is an ion mobility spectrum, there is no additional ionisation source required. In case the constituent parts of the sample are not or not necessarily ions like for example in the case where the spectrum to be determined is an aerosol mobility spectrum, a gas chromatography spectrum or a liquid chromatography spectrum, the detector preferably comprises an ionisation source for ionising the constituent parts of the sample.

As an example, a gas chromatography spectrum may be obtained with a gas chromatography spectrometer with a resolution in time of about 40 ms to 60 ms. In comparison, ion mobility spectrometers are faster. One entire measurement with an ion mobility spectrometer for example may take a time in a range of about 5 ms to 10 ms, thus enabling to perform every 5 ms to 10 ms a new measurement. An ion mobility spectrum obtained with one such measurement however can provide a resolution in time of about 300 µs. Mass spectrometer, in particular time-of-flight mass spectrometer, are even faster. One measurement with a mass spectrometer may take about 100 µs, enabling thus performing about every 100 µs a new measurement.

Thus, in a preferred variant, the method according to the invention is a method for determining a gas chromatography spectrum, while the detector is an ion mobility spectrometer. In this variant, the apparatus according to the invention is a gas chromatography spectrometer. In this case, the modulation time resolution is preferably in the range of about 40 ms to 60 ms, while the detection time resolution is preferably in the range of about 5 ms to 10 ms. Nonetheless, the modulation time resolution and the detection time resolution may differ from these values, too.

In another preferred variant, the method according to the invention is a method for determining an ion mobility spectrum, while the detector is a mass spectrometer, in particular a time-of-flight mass spectrometer. In this variant, the apparatus according to the invention is an ion mobility spectrometer. In this case, the modulation time resolution is preferably about 300 µs, while the detection time resolution is preferably in the range of about 100 µs. Nonetheless, the modulation time resolution and the detection time resolution may differ from these values, too.

In even another variant, the method according to the invention is a method for determining a gas chromatography spectrum and the apparatus according to the invention is a gas chromatography spectrometer. In this variant, the detector is an ion mobility spectrometer, which comprises itself as detection unit a mass spectrometer, in particular a time-of-flight mass spectrometer.

Independent of the type spectrum to be determined and independent of the type the apparatus according to the invention is, the apparatus according to the invention preferably comprises a control unit for controlling the modulation unit to divide the sample into assays for which the physical process or chemical process is initiated successively, timed according to the modulation pattern and for controlling the detector to start each cycle with a different offset in time as compared to the start of the modulation function the respective cycle is assigned to. This has the advantage that the apparatus can optimally be controlled.

Alternatively, the apparatus may not comprise such a control unit.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
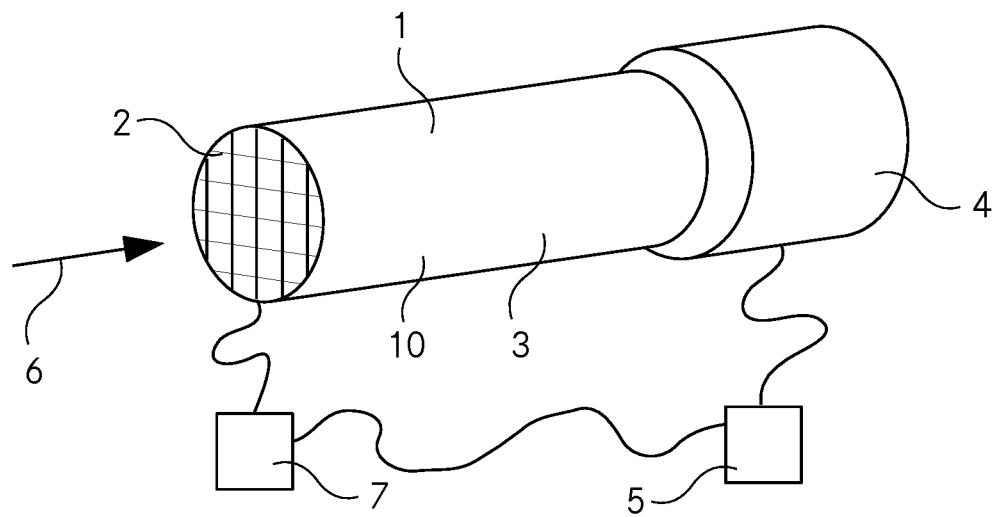
FIG. 1 a schematic view of an apparatus according to the invention in the form of an ion mobility spectrometer for executing the method according to the invention, FIG. 2 a schematic diagram of an experiment with the ion mobility spectrometer for determining an ion mobility spectrum with the method according to the invention, and FIG. 3 a schematic view of an apparatus according to the invention in the form of a gas chromatograph for executing the method according to the invention.

FIG. 1 shows a schematic view of an apparatus according to the invention in the form of an ion mobility spectrometer 1. This ion mobility spectrometer 1 may be used to execute a method according to the invention in order to determine an ion mobility spectrum.

The ion mobility spectrometer 1 comprises a modulation unit in the form of an ion gate 2, a drifting region 3, a detector in the form of a mass spectrometer 4 and a calculation unit 5. The drifting region 3 is confined by a tube 10. The ion gate 2 is arranged on an opposite end of the tube 10 than the mass spectrometer 4. The ion gate 2 is of a known type. It comprises a grid of wires. If a voltage with opposite signs is applied to neighbouring wires of the grid, ions of an ion beam 6 are prevented of entering the tube 10. If there is no voltage applied to the wires of the grid, the ions of the ion beam 6 may enter the tube 10. The switching of the ion gate 2 is controlled by a control unit 7. The ion gate 2 may be switched between an open state, where ions may pass the ion gate 2 and a closed state, where ions are prevented of passing the ion gate 2. Those ions of the ion beam 6 that pass the ion gate 2 enter the tube 10 and drift through the drifting region 3 to the mass spectrometer 4 which generates a detector signal. This detector signal is then passed to the calculation unit 5 for further processing.

In the present embodiment, the sample comprises as constituent parts the ions in the ion beam 6. How these ions and the ion beam 6 are generated is not of relevance for the present invention. The apparatus according to the invention may for example be fed with the ion beam 6 which may be a continuous ion beam. In another example, the apparatus according to the invention may comprise an ionisation source which ionises what is fed to the ionisation source in order to prepare the ion beam 6 from which the spectrum is to be determined. If for example the apparatus is itself used as a detector of an aerosol particle spectrometer, a gas chromatography spectrometer or a liquid chromatography spectrometer, the apparatus may comprise an ionisation source by which the aerosol particles, gas or liquid is transformed into the ion beam 6. For this transformation, the ionisation source of the apparatus may for example vaporise and ionise the aerosol particles, gas or liquid fed to the ionisation source. For example, the ionisation source may be a chemical ionisation source, a spark discharge ionisation source, a laser ionisation source, an extractive electrospray ionisation source or any other ionisation source known in the art.

In the present embodiment, the ion gate 2 works as modulation unit and modulates the ion beam 6 into a modulated ion beam. This modulated ion beam comprises batches or bunches of ions, the batches or bunches being assays comprising essentially the same distribution of constituent parts as the sample. In some embodiments, the distribution of constituent parts in the assays may change over time. This may for example be the case if the apparatus is itself used as a detector of an aerosol particle spectrometer, a gas chromatography spectrometer or a liquid chromatography spectrometer. Independent of whether the distribution changes over time, the physical process of passing the drifting region 3 is initiated for the assays by the ion gate 2 successively, timed according to a modulation pattern.

When performing a measurement, the ion gate 2 is controlled by the control unit 7 to switch according to the modulation pattern which is a function composed of N consecutive modulation functions with N being 2 or larger. These modulation functions are binary functions that may be represented as a sequence of bits having a value "1" or "0". A value "1" corresponds to the open state of the ion gate 2, while a "0" corresponds to the closed state of the ion gate 2. The modulation functions are maximum length sequences chosen such that their autocorrelation is a two-valued function that has a peak at zero and otherwise a constant value. The ion beam 6 approaches the ion gate 2 as a continuous ion beam. When entering the tube 10, it is modulated by the ion gate 2 to yield a modulated ion beam. In flight direction of the ions, this modulated ion beam has a shape that corresponds to the modulation pattern. The ions of the modulated ion beam are passed through the drifting region 3 and reach the mass spectrometer 4, which generates a detector signal. This detector signal is passed to the calculation unit 5, where a correlation of the signal and the modulation pattern is calculated. This correlation yields the ion mobility spectrum.

The mass spectrometer 4 is a time-of-flight mass spectrometer and is controlled by the control unit 7. It measures in N consecutive cycles the time when the ions have reached the mass spectrometer 4 and thus when they have completed the physical process of passing the drifting region 3. In succession of the cycles, each of the cycles is assigned to a consecutive one of the modulation functions within the modulation pattern. Each cycle is started with an offset in time as compared to a start of the modulation function it is assigned to. The mass spectrometer 4 provides mass spectra of the ions with a repetition rate of 100 µs. Each of these mass spectra comprises at the same time information on the number of ions which have passed the drifting region 3 and reached the mass spectrometer 4. Thus, the detector signal provided by the mass spectrometer 4 has a detection time resolution of 100 µs.

As mentioned, each cycle is started with an offset in time as compared to the start of the modulation function the respective cycle is assigned to. These offsets differ from each other. One of them is zero, while the other ones have an absolute value which is different from zero. Furthermore, they differ from the detection time resolution and from multiples of the detection time resolution.

Figure 2:
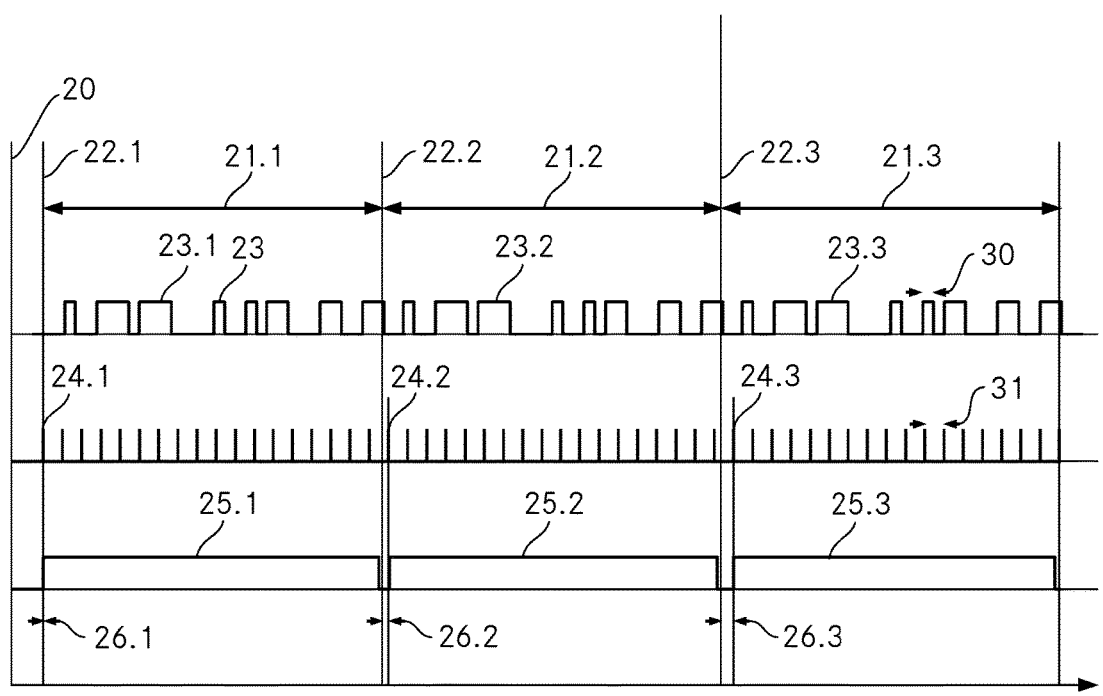

FIG. 2 shows a schematic diagram of an experiment with the ion mobility spectrometer 1 for determining an ion mobility spectrum with the method according to the invention. A horizontal axis of the diagram runs from left to right in the figure and represents the time axis of an experiment. On this time axis, the experiment is started at a start 20 indicated by a vertical line. A time gap after the start 20, the experiment is run down in three sequences 21.1, 21.2, 21.3. These sequences 21.1, 21.2, 21.3 all have a same length in time and thus take a same amount of time to run down. The start of each one of the sequences 21.1, 21.2, 21.3 is indicated with a vertical line in the diagram.

As described above, during the experiment, the ions are introduced by the ion gate 2 into the drifting region 3 modulated according to a modulation pattern 23. This modulation pattern 23 consists of three consecutive modulation functions 23.1, 23.2, 23.3. Thus, in the example of the diagram shown in FIG. 2, N is equal 3. Since the modulation functions 23.2, 23.2, 23.3 are binary functions that may be represented as a sequence of bits having a value "1" or "0", the modulation functions 23.1, 23.2, 23.3 are shown in the diagram as step-functions. Since FIG. 2 shows a schematic diagram, the modulation functions 23.1, 23.2, 23.3 are shown with steps for illustration purposes. In reality, these modulation functions 23.1, 23.2, 23.3 are longer and may each comprise 20 bits, 50 bits, 110 bits or even more bits. For this reason, the order of the bits of the modulation functions 23.1, 23.2, 23.3 shown in FIG. 2 are not correct. In order to obtain correct modulation functions, the person skilled in the art may use a linear feedback shift register and may employ the method disclosed in EP 2 587 259 A1 of Tofwerk AG, paragraphs 0058 to 0063 which is incorporated herein by reference. An addition to the linear feedback shift register or instead of the linear feedback shift register, the apparatus may comprise a store for storing one or more modulation functions which are used in the modulation pattern.

In the example shown in FIG. 2, the modulation functions 23.1, 23.2, 23.3 are identical to each other. They have a same length in time as the sequences 21.1, 21.2, 21.3 and they start 22.1, 22.2, 22.3 with the starts of the sequences 21.1, 21.2, 21.3.

The modulation functions 23.1, 23.2, 23.3 have a modulation time resolution 30 which is for all modulation functions 23.1, 23.2, 23.3 the same. It is the shortest time for which ions are continuously introduced by the ion gate 2 into the drifting region 3. Thus, the modulation time resolution 30 is the shortest time duration during which the physical process of passing ions through the drifting region 3 is initiated for one of the assays. In the present example, the modulation time resolution 30 is 300 µs.

Together with the start 22.1 of the first modulation function 23.1 in the modulation pattern 23, the detector in the form of the mass spectrometer 4 starts to measure the ions having passed the drifting region 3. For this measurement, the mass spectrometer 4 extracts every 100 µs for a few hundred nanoseconds the ions which have reached the end of the drifting region 3 into the mass spectrometer 4. In FIG. 2, these extractions 24.1, 24.2, 24.3 are illustrated as vertical bars. As compared to the modulation functions 23.1, 23.2, 23.3, only a zoom onto the time scale of the extractions 24.1, 24.2, 24.3 is shown in order to be able to recognise the time gaps between the extractions 24.1, 24.2, 24.3 which represent the detection time resolution 31 of 100 µs. Thus, in FIG. 2, the time scale of the time axis shown for the modulation functions 23.1, 23.2, 23.3 with the indicated modulation time resolution 30 of 300 µs is different from the time scale of the time axis shown for the detection time resolution 31 of 100 µs.

As mentioned already, the mass spectrometer 4 performs its measurements in N cycles 25.1, 25.2, 25.3, wherein N is equal 3 in the example of FIG. 2. Each of these cycles 25.1, 25.2, 25.3 is assigned to a consecutive one of the modulation functions 23.1, 23.2, 23.3 within the modulation pattern 23. Furthermore, each cycle 25.1, 25.2, 25.3 is started with an offset 26.1, 26.2, 26.3 in time as compared to the start 22.1, 22.2, 22.3 of the modulation function 23.1, 23.2, 23.3 the respective cycle 25.1. 25.2, 25.3 is assigned to. These offsets 26.1, 26.2, 26.3 differ from each other. The offset 26.1 of the first cycle 25.1 with respect to the start 22.1 of the first modulation function 23.1 within the modulation pattern 23 is zero. The offset 26.2 of the second cycle 25.2 with respect to the start 22.2 of the second modulation function 23.2 within the modulation pattern 23 is one third of the detection time resolution 31 of 100 µs, while the offset 26.3 of the third cycle 25.3 with respect to the start 22.3 of the third modulation function 23.3 within the modulation pattern 23 is two third of the detection time resolution 31 of 100 µs.

As mentioned already, the mass spectrometer 4 extracts into the mass spectrometer 4 every 100 µs for a few hundred nanoseconds the ions which have reached the end of the drifting region 3 since the last extraction. From each extraction, the mass spectrometer 4 obtains a mass spectrum of the ions. At the same time, the mass spectrometer 4 provides for each extraction information on the number of constituent parts of the sample that have completed the physical process of passing the drifting region 3 since the last extraction because the area below the mass spectrum is proportional to the number of ions detected by the mass spectrometer 4 in the respective extraction. Thus, the mass spectrometer 4 provides a detector signal which provides information on when what number of constituent parts have completed the physical process. This detector signal is an array of data points, wherein each data point provides information on the number of the constituent parts which have completed the physical process within a time interval assigned to the respective data point, wherein the time interval is the detection time resolution of 100 µs.

In order to calculate the correlation of the detector signal and the modulation pattern 23 with the calculation unit 5, each cycle 25.1, 25.2, 25.3 and the modulation function 23.1, 23.2, 23.3 the respective cycle 25.1, 25.2, 25.3 is assigned to are treated as an entity having a local timeline. In the illustration of FIG. 2, the sequences 21.1, 21.2, 21.3 can be considered as these entities. For each entity, the modulation function 23.1, 23.2, 23.3 of the respective entity preferably starts on the local timeline of the respective entity at a predetermined time which is for all entities zero. Thus, on the local timeline, the respective entity's cycle 25.1, 25.2, 25.3 starts at the respective cycle 25.1, 25.2, 25.3's offset 26.1, 26.2, 26.3 after the start 22.1, 22.2, 22.3 of the respective entity's modulation function 23.1, 23.2, 23.3. For calculating the correlation of the detector signal and the modulation pattern 23, the detector signal of each cycle 25.1, 25.2, 25.3 is preferably considered as a separate signal of the respective cycle 25.1, 25.2, 25.3 and thus of the entity the respective cycle 25.1, 25.2, 25.3 belongs to, wherein each of the separate signals starts with the corresponding cycle 25.1, 25.2, 25.3. This is achieved in that for the separate signal of each cycle 25.1, 25.2, 25.3, an initial delay corresponding to the respective cycle 25.1, 25.2, 25.3's offset 26.1, 26.2, 26.3 in time as compared to the start 22.1, 22.2, 22.3 of the modulation function 23.1, 23.2, 23.3 the respective cycle 25.1, 25.2, 25.3 is assigned to is prefixed to the separate signal of the respective cycle 25.1, 25.2, 25.3 before the correlation is calculated. Therefore, on the local timeline of an entity, the respective entity's modulation function 23.1, 23.2, 23.3 and the prefixed initial delay of the detector signal of the respective entity's cycle 25.1, 25.2, 25.3 starts at zero.

The correlation of the detector signal and the modulation pattern 23 is then calculated with the calculation unit 5 by first correlating for each entity the separate signal of the respective entity with the respective entity's modulation function 23.1, 23.2, 23.3 in order to obtain for each entity an array of data points, by second providing each array of data points on the local timeline of the respective entity and by third treating the local timelines of the entities as being the same and combining the data points of the obtained arrays to one array of data points which is the correlation. When correlating for each entity the separate signal of the respective entity with the respective entity's modulation function 23.1, 23.2, 23.3 in order to obtain for each entity an array of data points, the separate signals and modulation functions 23.1, 23.2, 23.3 are correlated by calculating a circular cross correlation. Instead of a circular cross correlation, an inverse Hadamard-transformation, a Fourier transformation, a Laplace transformation or an M-transformation or another formalism could be employed.

In a variant, the correlation of the detector signal and the modulation pattern 23 may be calculated with the calculation unit 5 in a different way. In this different way, first for each entity the separate signal of the respective entity on the local timeline of the respective entity is provided, second the local timelines of the entities are treated as being the same and the separate signals of the entities are combined to one virtual signal and third the virtual signal with one of the modulation functions 23.1, 23.2, 23.3 within the modulation pattern 23 are correlated. When correlating the virtual signal with one of the modulation functions 23.1, 23.2, 23.3 within the modulation pattern, the virtual signal and the modulation function 23.1, 23.2, 23.3 are correlated by calculating a circular cross correlation. Instead of a circular cross correlation, an inverse Hadamard-transformation, a Fourier transformation, a Laplace transformation or an M-transformation or another formalism could be employed.

In either variant, the data points of the obtained arrays or the separate signals, respectively, are provided on the local timeline of their respective entity when being combined, while the local timelines are treated as being the same. Thus, treating the local timelines as being the same and combining the data points or separate signals, respectively, means using the values of the positions of the data points or of the separate signals, respectively, which refer to the respective local timeline, and applying these values to a new, globally valid timeline.

In the embodiment illustrated in FIG. 2, the first data point of the first sequence 22.1 is provided by the first extraction 24.1 of the mass spectrometer 4 during the first cycle 25.1. This first extraction 24.1 starts with the offset 26.1 of zero after the start 22.1 of the first modulation function 23.1 and thus at zero on the local timeline of the first sequence 22.1. The second extraction of the mass spectrometer 4 during the first cycle 25.1 is 100 µs later. Thus, the second data point of the first sequence 22.1 is on the local timeline at 100 µs.

Furthermore, in FIG. 2, the first data point of the second sequence 22.2 is provided by the first extraction 24.2 of the mass spectrometer 4 during the second cycle 25.2. This first extraction 24.2 starts with the offset 26.2 of 33.3 µs after the start 22.2 of the second modulation function 23.2 and thus at 33.3 µs on the local timeline of the second sequence 22.2. The second extraction of the mass spectrometer 4 during the second cycle 25.2 is 100 µs later. Thus, the second data point of the second sequence 22.2 is on the local timeline at 133.3 µs.

Furthermore, in FIG. 2, the first data point of the third sequence 22.3 is provided by the first extraction 24.3 of the mass spectrometer 4 during the third cycle 25.3. This first extraction 24.3 starts with the offset 26.3 of 66.6 µs after the start 22.3 of the third modulation function 23.3 and thus at 66.6 µs on the local timeline of the third sequence 22.3. The second extraction of the mass spectrometer 4 during the third cycle 25.3 is 100 µs later. Thus, the second data point of the third sequence 22.3 is on the local timeline at 166.6 µs.

As mentioned already, during the calculation of the correlation, at some point data points are combined to one array of data points or to one virtual signal with a globally valid timeline. In case of the embodiment illustrated in FIG. 2, the resulting array of data points or virtual signal starts as follows: The first data point located at time zero and originates from the first data point of the first sequence 21.1. The second data point is located at 33.3 µs and originates from the first data point of the second sequence 21.2. The third data point is located at 66.6 µs and originates from the first data point of the third sequence 21.3. The fourth data point is located at 100 µs and originates from the second data point of the first sequence 21.1. The fifth data point is located at 133.3 µs and originates from the second data point of the second sequence 21.2, while the sixth data point is located at 166.6 µs and originates from the second data point of the third sequence 21.3. Thus, the data points originating from the different sequences 21.1, 21.2, 21.3 are interlocked when being combined.

Since the finally obtained correlation is based on the interlocked data points originating from the different sequences 21.1, 21.2, 21.3 during the experiment, the finally obtained correlation provides a better resolution in time than the detection time resolution 31 used during the experiment.

Figure 3:
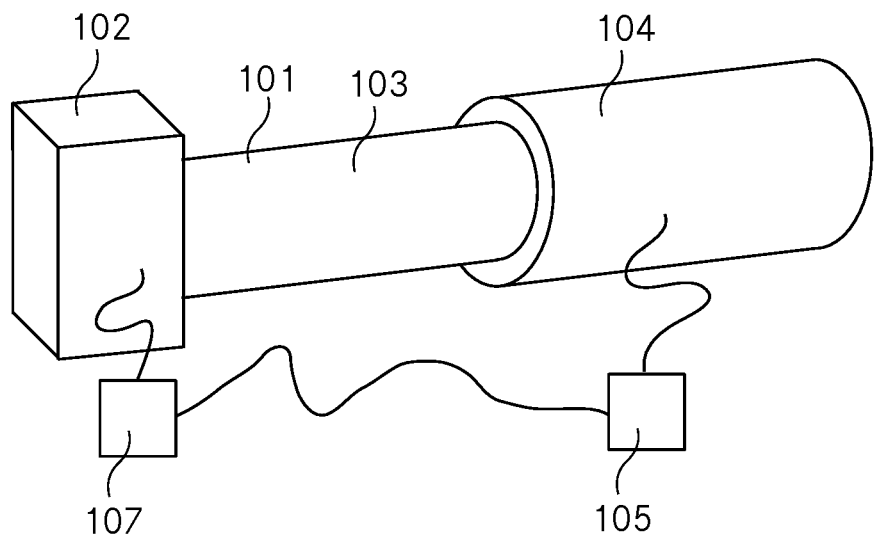

FIG. 3 shows a schematic view of an apparatus according to the invention in the form of a gas chromatograph 101 for executing the method according to the invention in order to determine a gas chromatogram. This gas chromatogram is a spectrum in the sense of the present invention because it is an array of data points and represents the one or more constituent parts of the sample ordered in accordance with the magnitudes of a common physical property which is the time the constituent parts require to pass the gas chromatography column. Each data point of the gas chromatogram is assigned to a particular time or range of time the constituent parts may require to pass the gas chromatography column and each data point indicates the amount of constituent parts in the sample which effectively required the time or range of time assigned to the respective data point to pass the gas chromatography column.

The gas chromatograph 101 provides gas chromatograms of gaseous samples. It comprises an injection nozzle 102, a gas chromatography column 103, an ion mobility spectrometer 104, a calculation unit 105 and a control unit 107. The injection nozzle 102 is arranged on one end of the gas chromatography column 103 and is used for dividing the sample into assays by injecting pulses of gas successively, timed according to a modulation pattern into the gas chromatography column 103. Thus, the physical process of passing the gas chromatography column 103 is initiated by the injection nozzle 102 which works as modulation unit. The ion mobility spectrometer 104 is arranged at the opposite end of the gas chromatography column 103 than the injection nozzle 102 and measures the time when the constituent parts of the sample have passed the gas chromatography column 103. This ion mobility spectrometer 104 generates a detector signal which is passed to the calculation unit 105 for further processing. The ion mobility spectrometer 104 may be any ion mobility spectrometer 104 known in the art or may be the ion mobility spectrometer 1 described above in the context of FIGS. 1 and 2.

Instead of the injection nozzle 102, the gas chromatograph 101 may comprise a different modulation unit. In case the gas chromatograph 101 for example provides gas chromatograms of liquid samples, the sample may be divided into assays by an injection unit which injects the assays successively, timed according to the modulation pattern into an evaporation chamber or directly into the gas chromatography column 103 if the evaporation chamber is integrated in the gas chromatography column 103. In that case, the physical process of passing the gas chromatography column 103 is initiated in the evaporation chamber by evaporating the liquid. In another variant, the entire sample may be introduced into the evaporation chamber in one go. In this variant, the sample may be divided into assays by a heating device which heats the sample with heating pulses timed according to the modulation pattern. Thus, the employed heating device forms the modulation unit and initiates the physical process of passing the gas through the gas chromatography column 103.

When performing a measurement, the injection nozzle 102 is controlled by the control unit 107 to inject gas into the gas chromatography column 103 modulated according to a function composed of N consecutive modulation functions with N being 2 or larger. These modulation functions are binary functions that may be represented as a sequence of bits having a value "1" or "0". A value "1" corresponds to injecting of gas, while a "0" corresponds to not injecting gas. The modulation functions are maximum length sequences chosen such that their autocorrelation is a two-valued function that has a peak at zero and otherwise a constant value. The gas which has passed the gas chromatography column 103 and reaches the ion mobility spectrometer 104 is detected by the ion mobility spectrometer 104 which generates a detector signal. This detector signal is passed to the calculation unit 105, where a correlation of the signal and the modulation pattern is calculated. This correlation yields the gas chromatogram.

The ion mobility spectrometer 104 is controlled by the control unit 107. It measures in N consecutive cycles the time when the gas has reached the ion mobility spectrometer 104 and thus when the gas has completed the physical process of passing the gas chromatography column 103. In succession of the cycles, each of the cycles is assigned to a consecutive one of the modulation functions within the modulation pattern. Each cycle is started with an offset in time as compared to a start of the modulation function it is assigned to. The ion mobility spectrometer 104 provides an ion mobility spectrum with a repetition rate of 7 ms. Each of these ion mobility spectra comprises at the same time information amount of gas which has passed the gas chromatography column 103 and reached the ion mobility spectrometer 104. Thus, the detector signal provided by the ion mobility spectrometer 104 has a detection time resolution of 7 ms.

As mentioned, each cycle is started with an offset in time as compared to the start of the modulation function the respective cycle is assigned to. These offsets differ from each other. One of them is zero, while the other ones have an absolute value which is different from zero. Furthermore, they differ from the detection time resolution and from multiples of the detection time resolution.

How an experiment with the gas chromatograph 101 for determining a gas chromatogram with the method according to the invention is performed is very similar to the experiment with the ion mobility spectrometer 1 for determining an ion mobility spectrum as illustrated in FIG. 2. Most explanations provided above with respect to FIG. 2 apply for the gas chromatography experiment. In the gas chromatography experiment however, the detection time resolution is 7 ms. Furthermore, the modulation time resolution is 50 ms.

The invention is not limited to the above described ion mobility spectrometer 1 and method for determining an ion mobility spectrum and the above described gas chromatograph 101 and method for determining a gas chromatogram. For example, N may be different from 3. For example, N may be 2, 4, 5, 6, 7, 8, 9, 10 or larger than 10. Furthermore, the detection time resolution and the modulation time resolution may differ from the indicated values. Additionally, the modulation functions within the modulation pattern may be different from each other. They may have a same length or may have different lengths.

Instead of an ion mobility spectrum or a gas chromatogram, the type of spectrum to be determined with the apparatus and the method according to the invention may for example be an aerosol mobility spectrum, a liquid chromatography spectrum or another type of spectrum. Furthermore, the detector employed in the apparatus and the method according to the invention may be a different type of spectrometer than an ion mobility spectrometer or a mass spectrometer. Furthermore, the detector may be no spectrometer but just a detector.

Additionally, the spectrum to be determined by the apparatus and the method according to the invention may be based on the time the one or more constituent parts of the sample require to undergo a chemical process instead of a physical process. Such a chemical process may for example be the time the one or more constituent parts of the sample require to undergo a specific chemical reaction.

In summary, it is to be noted that a method and an apparatus are provided that enable determining a spectrum with a better resolution and a high data collection rate.

The invention claimed is:

1. A method for determining a spectrum of a sample comprising one or more constituent parts on the basis of a time required for the one or more constituent parts to undergo a physical process or chemical process, wherein the spectrum is determined by:
   a) dividing the sample by a modulation unit into assays for which the physical process or chemical process is initiated successively, timed according to a modulation pattern which is a function composed of N consecutive modulation functions with N being an integer value 2 or larger;
   b) measuring with a detector in N consecutive cycles a time when the constituent parts of the sample have completed the physical process or chemical process, wherein in succession of the cycles, each cycle is assigned to a consecutive one of the modulation functions within the modulation pattern, wherein each cycle is started with an offset in time as compared to a start of the modulation function it is assigned to, wherein for each cycle, the offset is different, wherein the detector provides a detector signal providing information on when what number of constituent parts have completed the physical process or chemical process and wherein the detector signal has a detection time resolution, wherein at least one of the offsets has an absolute value different from zero, different from the detection time resolution and different from multiples of the detection time resolution; and c) calculating a correlation of the detector signal and the modulation pattern with a calculation unit.

2. The method according to claim 1, wherein for each modulation function within the modulation pattern, an autocorrelation of the respective modulation function is a two-valued function, wherein the autocorrelation has a peak at zero and a constant value at all other points.

3. The method according to claim 1, wherein each modulation function within the modulation pattern is a binary function.

4. The method according to claim 1, wherein each modulation function within the modulation pattern is a pseudo-random sequence.

5. The method according to claim 4, wherein each modulation function within the modulation pattern is a maximum length sequence, a GMW sequence, a Welch-Gong transformation sequence, a Quadratic residue sequence, a Sextic residue sequence, a Twin prime sequence, a Kasami power function sequence, a Hyperoval sequence or a sequence derived from 3 or 5 maximum length sequences.

6. The method according to claim 1, wherein the offsets differ from each other, wherein a difference between any two of the offsets is one fraction of the detection time resolution or a multiple of the one fraction of the detection time resolution.

7. The method according to claim 1, wherein the detection time resolution of the detector signal of each cycle is the same.

8. The method according to claim 1, wherein the correlation is calculated by calculating a circular cross correlation, an inverse Hadamard-transformation, a Fourier transformation, a Laplace transformation or an M-transformation.

9. The method according to claim 1, wherein for calculating the correlation of the detector signal and the modulation pattern, each cycle and the modulation function the respective cycle is assigned to are treated as an entity having a local timeline, wherein for each entity, the modulation function of the respective entity starts on the local timeline of the respective entity at a predetermined time which is for all entities the same, wherein the detector signal of each cycle is considered as a separate signal of the respective cycle and thus of the entity the respective cycle belongs to, wherein each of the separate signals starts with the corresponding cycle, wherein the correlationr of the detector signal and the modulation pattern is calculated with the calculation unit a) by first correlating for each entity the separate signal of the respective entity with the respective entity's modulation function in order to obtain for each entity an array of data points, by second providing each array of data points on the local timeline of the respective entity and by third treating the local timelines of the entities as being the same and combining the data points of the obtained arrays to one array of data points which is the correlation; or b) by first providing for each entity the separate signal of the respective entity on the local timeline of the respective entity, by second treating the local timelines of the entities as being the same and combining the separate signals of the entities to one virtual signal and by third correlating the virtual signal with one of the modulation functions within the modulation pattern, wherein the modulation functions within the modulation pattern are the same.

10. The method according to claim 1, wherein each modulation function within the modulation pattern has a modulation time resolution.

11. The method according to claim 1, wherein the modulation time resolution is at least three times larger than the detection time resolution.

12. The method according to claim 1, wherein the spectrum is an ion mobility spectrum, an aerosol mobility spectrum, a gas chromatography spectrum or a liquid chromatography spectrum.

13. The method according to claim 1, wherein the detector is an ion mobility spectrometer or a mass spectrometer.

14. An apparatus for determining a spectrum of a sample comprising one or more constituent parts on the basis of the time the one or more constituent parts require to undergo a physical process or chemical process, wherein the apparatus comprises:

a) a modulation unit for dividing the sample into assays for which the physical process or chemical process is initiatable successively, timed according to a modulation pattern which is a function composed of N consecutive modulation functions with N being an integer value 2 or larger;

b) a detector for measuring in N consecutive cycles a time when the constituent parts of the sample have completed the physical process or chemical process, wherein in succession of the cycles, each cycle is assigned to a consecutive one of the modulation functions within the modulation pattern, wherein the detector enables starting each cycle with an offset in time as compared to a start of the modulation function it is assigned to, wherein for each cycle, the offset is different, wherein a detector signal is providable by the detector, the detector signal providing information on when what number of the constituent parts have completed the physical process or chemical process, wherein the detector signal has a detection time resolution, wherein at least one of the offsets has an absolute value different from zero, different from the detection time resolution and different from multiples of the detection time resolution; and c) a calculation unit for calculating a correlation of the detector signal and the modulation pattern.

15. The apparatus according to claim 14, wherein the apparatus comprises a control unit for controlling:

a) the modulation unit to divide the sample into assays for which the physical process or chemical process is initiated successively, timed according to the modulation pattern and b) the detector to start each cycle with a different offset in time as compared to the start of the modulation function the respective cycle is assigned to.

16. The method according to claim 2, wherein each modulation function within the modulation pattern is a binary function.

17. The method according to claim 10, wherein the modulation time resolution is at least five times larger than the detection time resolution.

18. The method according to claim 10, wherein the modulation time resolution is at least seven times or ten times larger than the detection time resolution.

19. The method according to claim 1, wherein the detector is a time-of-flight mass spectrometer.

\* \* \* \* \*